United States Patent [19]

Chang

[11] 4,014,744
[45] Mar. 29, 1977

[54] PROCESSES FOR MEASURING TRI-, DI- AND MONOGLYCERIDES

[75] Inventor: Eppie Sheng Chang, Elkhart, Ind.

[73] Assignee: Miles Laboratories Inc., Elkhart, Ind.

[22] Filed: Jan. 30, 1975

[21] Appl. No.: 545,703

[52] U.S. Cl. .................. 195/103.5 R; 260/417
[51] Int. Cl.$^2$ ............................ G01N 31/14
[58] Field of Search .......... 195/103.5 R; 23/230 B; 260/398, 417

[56] References Cited

UNITED STATES PATENTS

| 3,703,591 | 11/1972 | Bucolo et al. | 195/103.5 R |
| 3,862,009 | 1/1975 | Wahlefeld et al. | 195/103.5 R |

OTHER PUBLICATIONS

D. L. Horney, "An Approach to the Measurement of Total Lipid Glycerol in Serum", Clin. Chem. 19/5, pp. 453–458 (1973).

Primary Examiner—A. Louis Monacell
Assistant Examiner—C. A. Fan
Attorney, Agent, or Firm—E. H. Gorman, Jr.

[57] ABSTRACT

In processes for measuring glycerides in a fluid, which processes require initial conversion thereof to glycerol, this conversion is achieved according to an improved and simplified saponifying reaction in which a reaction temperature between 35° and 40° C. is used.

8 Claims, No Drawings

PROCESSES FOR MEASURING TRI-, DI- AND MONOGLYCERIDES

BACKGROUND OF THE INVENTION

This invention relates to processes for measuring glycerides in a fluid. More particularly, this invention regards an improved method for converting glycerides to glycerol when such conversion is required by the process used for measuring glycerides in the fluid.

It is recognized that there is a need for an inexpensive and an efficient process of measuring glycerides in fluids. Such a process is particularly desired for measuring glycerides in fluids such as human serum or plasma where their presence may indicate pathological conditions such as atherosclerosis, ischemic heart disease, myocardial infarction, fat induced or carbohydrate induced triglyceridemia, diabetes mellitus, fatty infiltration of the liver and certain glycogen storage diseases.

It was known to measure glycerides in fluids by first converting the glycerides to glycerol and then further reacting the glycerol in a series of enzymatic reactions to form a product having color characteristics measurable with a spectrophotometer or a colorimeter. These measurements were then converted to concentrations of glycerides with an appropriate graph, table, etc.

An example of such an enzymatic conversion procedure is set forth in the following reaction sequence in which the final product is pyruvate.

Abbreviations used herein

ATP = adenosine — 5' — triphosphate
GK = glycerol kinase
GP = α — glycerol phosphate
ADP = adenosine — 5' — diphosphate
PEP = phosphoenolpyruvate
PK = pyruvate kinase
NADH$_2$ = nicotinamide adenine dinucleotide (reduced)
NAD = nicotinamide adenine dinucleotide (oxidized)

The resulting pyruvate was then further reacted to form either a colored reaction product or a colorless reaction product. For example, pyruvate was reacted with NADH$_2$ in the presence of lactate dehydrogenase to form lactate and NAD. Such a procedure is described in R. Richterich, *Clinical Chemistry, Theory and Practice*, Academic Press, New York, pp 270–278.

It was an accepted practice to convert glycerides in fluids to glycerol with a high temperature saponification utilizing an alcoholic-alkaline saponifying reagent. This saponification was performed by maintaining a mixture of the fluid and the saponifying reagent at a temperature between 60° and 80° C. for about 30 minutes. Such a procedure is described in R. Richterich, *Clinical Chemistry, Theory and Practice*, ibid.

More recently, conversion of glycerides to glycerol was accomplished with an enzymatic procedure as described in U.S. Pat. Nos. 3,703,591 and 3,759,793. Of course, this latter procedure requires use of particular enzymes suitable for accomplishing the desired conversion.

SUMMARY OF THE INVENTION

This invention is embodied in an improvement in processes for measuring glycerides in fluids in which processes a conversion of the glycerides to glycerol is required. The improvement is characterized in a saponification of the glycerides to glycerol with an ethanol-potassium hydroxide saponifying reagent at a temperature of between 35° and 40° C.

It is an object of this invention to substantially reduce the temperature of saponification of glycerides to glycerol in a process for measuring glycerides in fluids.

A further object of this invention is to shorten the time required for conversion of glycerides to glycerol in a process for measuring glycerides in fluids.

DESCRIPTION OF THE INVENTION

In this invention, a quantity of a fluid to be measured for glycerides is mixed with an ethanol-potassium hydroxide saponifying reagent and incubated at a temperature between about 35° and 40° C. until a substantial amount of the glycerides therein is saponified to glycerol.

It has unexpectedly been found that with the temperature used for the saponification of the glycerides reduced as much as about 68%, based upon room temperature as a base temperature, the measured amounts thereof in fluids are statistically the same as amounts determined with previously known processes which required high temperature saponification.

With the low temperature saponification of this invention, conversion of glycerides to glycerol is completed in a period of time which is significantly shorter than reaction periods generally practiced with high temperature saponifications. It has been discovered that this conversion is substantially complete in as little as 12 minutes. In such a short period of time a ninety percent recovery of glycerides in a fluid has been consistently observed. Of course, the incubation period of the saponification may extend for longer periods of time without adversely affecting the accuracy of the measurement of the glycerides.

The saponifying reagent is the well known ethanol-potassium hydroxide solution. Typically, such a solution is from 0.5N to and including 0.7N KOH in 90–95% ethanol or in enough water to solubilize the KOH.

The glycerol thus obtained may then be further reacted in accordance with reaction sequences of known processes which are used for measuring glycerides in fluids. Certain of these processes have been previously mentioned and will not, therefore, be considered further herein.

It has been found advantageous to adjust the pH of the mixtures of the fluid and the saponifying reagent following saponification of the glycerides to glycerol by adding thereto a metal salt which forms a precipitate with OH ions therein. Preferred salts for forming this precipitate are those which liberate Mg++ ions in solution such as MgSO$_4$. It has been found advantageous to employ an MgSO$_4$ concentration of between 0.1M to 0.112M inclusive in the reagent mixture.

It is also beneficial to add a filtering agent, such as a microcrystalline cellulose, with the pH adjusting salt. This agent enhances the preparation of the glycerol mixture for subsequent processing. It is believed that the filtering agent aids in entrapment of the precipitate and other undesirable molecules that might interfere with final color development.

A preferred process of rapid and accurate measurement of glycerides in fluids after conversion thereof to glycerol according to this invention utilizes the following reaction sequence.

In this reaction sequence 2,4-dinitrophenylhydrazine (DNPH) is used as a chromogen to react with pyruvate to form a colored product, pyruvate-dinitrophenylhydrazone (P-DNPH), which is brownish in a basic pH. The absorbance by P-DNPH is readily determined with a colorimeter at between 530 and 550 nm.

The process of this invention and its practice will be further described in the following example which sets forth measurements of glycerides in ten fluid samples. It is understood that although the fluid in this example is serum, the improvement of this invention may be used equally well with other fluids, such as plasma, containing glycerides. This example is merely representative of this invention and does not limit the scope or use thereof in any way.

DESCRIPTION OF THE PREFERRED EMBODIMENTS OF THE INVENTION

EXAMPLE

In this Example, the amount of glycerides in each of ten serum samples was measured according to the procedure of this invention and, as a reference assay, according to the procedure of Fletcher, Margaret J; A Colorimetric Method for Estimating Serum Triglycerides, *Clin. Chem. Acta*, 22:393, 1968.

These serums were obtained from laboratory personnel working with the inventors.

Standard reagents used in this procedure were:
1. Saponifying Reagent: 0.5N KOH in 90% ethanol
2. Reaction Mixture: A dry mixture, consisting of the following, was reconstituted with 27 ml. of distilled water.
   ATP 6 mg
   PEP 10 mg
   PK 30 I.U. (International Units)
   GK 12 I.U. (International Units)
   Dithioerythritol 00.001M
   Dextran (molecular weight 500,000) 135 mg.
   0.025M Tris-HCl pH 7.6
3. Color reagent: 0.05% 2,4-dinitrophenylhydrazine in 1N hydrochloric acid.
4. pH adjuster: 8N NaOH To 0.5 ml. of each serum 2.2 ml. of saponifying reagent was added and mixed well. This mixture was incubated at 37° C. for 12 minutes. The incubated mixture was added to 5.3 ml. of an aqueous 0.1M MgSO$_4$ solution and 0.3 gm. of a microcrystalline cellulose (AVICEL) and vigorously shaken. This latter combination was allowed to rest for 5 minutes and then filtered with a glass filter. To 1.3 ml. of the filtrate, 2.7 ml. of the reaction mixture was added, mixed well and incubated at 37° C. for 12 minutes. The color reagent (1 ml.) was added to the incubated filtrate mixture and allowed to stand for 5 minutes after which 0.3 ml. of the pH adjuster were added and mixed thoroughly therewith.

The final mixture stood for 5 minutes at room temperature, about 22° C., at which time the absorbance was measured at 550 nm. with a spectrophotometer. The observed absorbances and amounts of glycerides measured with the reference assay are set forth in the following Table:

TABLE

| Sample Number | Ref. Assay mg % | Procedure of Example |
|---|---|---|
| 1 | 42 | 0.250 |
| 2 | 85 | 0.323 |
| 3 | 262 | 0.634 |
| 4 | 440 | 0.913 |
| 5 | 102 | 0.363 |
| 6 | 254 | 0.601 |
| 7 | 47 | 0.268 |
| 8 | 70 | 0.304 |
| 9 | 176 | 0.504 |
| 10 | 709 | 1.342 |

A plot of the concentrations in mg % obtained by the reference assay against the absorbances observed with the procedure of this example resulted in a substantially linear relationship. Therefore, it is concluded that the amount of glycerides measured in a sample according to a process in which such glycerides are saponified to glycerol according to the procedure of this invention is substantially the same as the amount determined by the reference assay.

From the foregoing it is clear that this invention has improved and simplified processes for measuring glycerides in fluids and that a person skilled in the art will recognize how to use this invention.

What is claimed is:

1. In a process for measuring glycerides in a fluid in which substantially all of the glycerides are saponified to glycerol with an ethanol-potassium hydroxide saponifying reagent, the improvement which consists of effecting saponification by incubating a combination of the fluid and the saponifying reagent at a temperature between 35 and 40° C. until said saponification is substantially complete.

2. A process according to claim 1 in which said mixture is incubated for at least 12 minutes.

3. A process according to claim 1 in which said fluid is serum.

4. A process according to claim 1 in which said fluid is plasma.

5. A process according to claim 1 including as subsequent steps mixing a filtering agent and a metal salt with the saponified mixture and filtering the resulting combination to form a clear filtrate.

6. A process according to claim 5 in which said metal salt is MgSO$_4$.

7. A process according to claim 6 including as subsequent steps mixing said filtrate with GK and ATP to form GP and ADP, mixing said GP and ADP with PEP and PK to form ATP and pyruvate, adding DNPH to said pyruvate and ATP to form a mixture including P-DNPH, adding a base to said mixture to obtain a basic pH and measuring the absorbance of the final mixture.

8. A process according to claim 7 in which the absorbance is measured colorimetrically between 530 and 550 nm.

* * * * *